United States Patent
Bezemer

(10) Patent No.: US 9,980,650 B2
(45) Date of Patent: May 29, 2018

(54) SYSTEM AND METHOD FOR DETERMINING VITAL SIGN INFORMATION OF A SUBJECT

(71) Applicant: KONINKLIJKE PHILIPS N.V., Eindhoven (NL)

(72) Inventor: Rick Bezemer, Amsterdam Zuidoost (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 106 days.

(21) Appl. No.: 14/764,588

(22) PCT Filed: Feb. 4, 2014

(86) PCT No.: PCT/IB2014/058781
§ 371 (c)(1),
(2) Date: Jul. 30, 2015

(87) PCT Pub. No.: WO2014/122577
PCT Pub. Date: Aug. 14, 2014

(65) Prior Publication Data
US 2015/0366455 A1 Dec. 24, 2015

Related U.S. Application Data

(60) Provisional application No. 61/760,683, filed on Feb. 5, 2013.

(30) Foreign Application Priority Data

Feb. 5, 2013 (EP) ..................................... 13154017

(51) Int. Cl.
*A61B 5/00* (2006.01)
*A61B 5/0205* (2006.01)
(Continued)

(52) U.S. Cl.
CPC .......... *A61B 5/0077* (2013.01); *A61B 5/0004* (2013.01); *A61B 5/0059* (2013.01);
(Continued)

(58) Field of Classification Search
CPC .... A61B 2090/3945; A61B 2560/0412; A61B 2562/0233; A61B 2562/08; A61B 5/0004;
(Continued)

(56) References Cited

U.S. PATENT DOCUMENTS 8,106,344 B2 1/2012 Tamaki et al.
2013/0303921 A1* 11/2013 Chu .................. A61B 5/02416
600/473

FOREIGN PATENT DOCUMENTS

| CN | 102697487 A | 10/2012 |
|---|---|---|
| JP | 2011147469 | 8/2011 |

(Continued)

OTHER PUBLICATIONS

Cennini, G., et al.; Heart rate monitoring via remote photoplethysmography with motion artifacts reduction; 2010; Optics Express; 18(5)4867-4875.
(Continued)

*Primary Examiner* — Amanda Patton

(57) ABSTRACT

A remote photoplethysmography system includes a filter (10) for application to a detection unit. The filter further includes a first filter area (11) configured to transmit light (A) at a first wavelength and a second filter area (12) configured to transmit light (D) at a second wavelength. The detection unit (22) detects radiation received from the first filter area and from the second filter area of the filter. An analysis unit (6) determines the vital sign information of the subject from the detected radiation from the first filter area and from the second filter area.

15 Claims, 6 Drawing Sheets

(51) Int. Cl.
*A61B 5/026* (2006.01)
*A61B 5/1455* (2006.01)
*A61B 5/024* (2006.01)
*A61B 90/00* (2016.01)

(52) U.S. Cl.
CPC ........ *A61B 5/0082* (2013.01); *A61B 5/02055* (2013.01); *A61B 5/0261* (2013.01); *A61B 5/14551* (2013.01); *A61B 5/14552* (2013.01); *A61B 5/6842* (2013.01); *A61B 5/6898* (2013.01); *A61B 5/7278* (2013.01); *A61B 90/39* (2016.02); *A61B 5/0024* (2013.01); *A61B 5/02416* (2013.01); *A61B 5/6833* (2013.01); *A61B 2090/3945* (2016.02); *A61B 2560/0412* (2013.01); *A61B 2562/0233* (2013.01); *A61B 2562/08* (2013.01)

(58) Field of Classification Search
CPC ... A61B 5/0024; A61B 5/0059; A61B 5/0077; A61B 5/0082; A61B 5/02055; A61B 5/02416; A61B 5/0261; A61B 5/14551
See application file for complete search history.

(56) References Cited

FOREIGN PATENT DOCUMENTS

| | | |
|---|---|---|
| WO | 2012099536 A1 | 7/2012 |
| WO | 2013030745 A1 | 3/2013 |

OTHER PUBLICATIONS

Wieringa, F. P., et al.; Contactless Multiple Wavelength Photoplethysmograhpic Imaging: A First Step Toward SpO2 Camera Technology; 2005; Annals of biomedical Engineering; 33(8)1034-1041.

\* cited by examiner

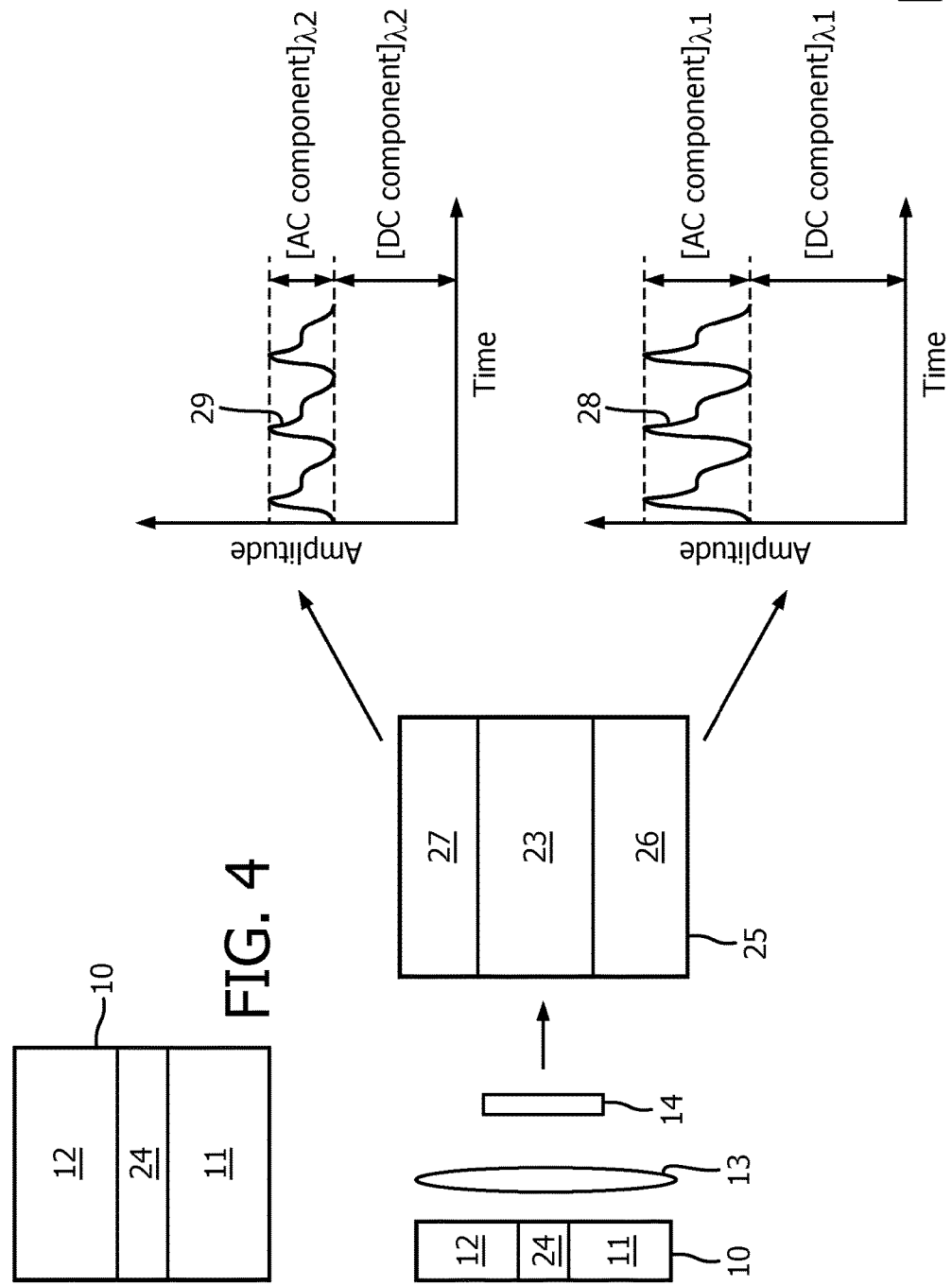

SYSTEM AND METHOD FOR DETERMINING VITAL SIGN INFORMATION OF A SUBJECT

CROSS REFERENCE TO RELATED APPLICATIONS

This application is a national filing of PCT application Serial No. PCT/IB2014/058781, filed Feb. 4, 2014, published as WO 2014/122577 A1 on Aug. 14, 2014, which claims the benefit of U.S. provisional application Ser. No. 61/760,683 filed Feb. 5, 2013 and EP provisional application serial no. 13154017.1 filed Feb. 5, 2013, both of which are incorporated herein by reference.

FIELD OF THE INVENTION

The present invention relates to a system and method for determining vital sign information of a subject. In particular, the present invention relates to optical measurement approaches which can be used for remotely determining vital signs of an observed subject. In this context, optical measurement may refer to photo-plethysmography (PPG) and, more specifically, to pulse oximetry.

BACKGROUND OF THE INVENTION

Vital signs of a person, for example the heart rate (HR), the respiration rate (RR) or the blood oxygen saturation, serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heart beat.

Photoplethysmography (PPG) is an optical measurement technique that evaluates a time-variant change of light reflectance or transmission of an area or volume of interest. PPG is based on the principle that blood absorbs light, so variations in blood volume with every heart beat affect transmission or reflectance correspondingly. Besides information about the heart rate, a PPG waveform can comprise information attributable to further physiological phenomena such as the respiration. By evaluating the transmissivity and/or reflectivity at different wavelengths (typically red and infrared), the blood oxygen saturation can be determined.

Conventional pulse oximeters for measuring the heart rate and the oxygen saturation of a subject are attached to the skin of the subject, for instance to a finger tip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmissivity of the same area or volume of tissue at two different wavelengths. This is referred to as time-division-multiplexing. The transmissivity over time at each wavelength gives the PPG waveforms for red and infrared wavelengths. Although contact PPG is regarded as a basically non-invasive technique, contact PPG measurement is often experienced as being unpleasant, since the pulse oximeter is directly attached to the subject and any cables limit the freedom to move.

Recently, non-contact, remote PPG devices for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications.

Wieringa, et al., "*Contactless Multiple Wavelength Photoplethysmographic Imaging: A First Step Toward "SpO2 Camera" Technology*," Ann. Biomed. Eng. 33, 1034-1041 (2005), discloses a remote PPG system for contactless imaging of arterial blood oxygen saturation in tissue based upon the measurement of plethysmographic signals at different wavelengths. The system comprises a monochrome CMOS-camera and a light source with LEDs of three different wavelengths. The camera sequentially acquires three movies of the subject. During each movie, the subject is illuminated by the light source at a different wavelength. The pulse rate can be determined from a movie at a single wavelength, whereas at least two movies at different wavelengths are required for determining the oxygen saturation. The measurements are performed in a darkroom, using only one wavelength at a time. The patient is not allowed to move between the subsequent measurements at different wavelengths. A further problem is that a measurement in darkness is not practical for unobtrusive medical and non-medical applications.

SUMMARY OF THE INVENTION

It is an object of the present invention to provide an improved system and method for unobtrusively and economically determining vital sign information of a subject. It would be advantageous to provide a system and method for operation under ambient light conditions. Further advantageously the system and method enable parallel and possibly real-time measurement of the heart rate and oxygen saturation.

In a first aspect of the present invention a system for determining vital sign information of a subject is presented that comprises a marker for application to a detection unit, said marker further comprising a first marker area configured to transmit light at a first wavelength and a second marker area configured to transmit light at a second wavelength, the detection unit for detecting radiation received from the first marker area and from the second marker area of the marker, and an analysis unit for determining the vital sign information of the subject from the detected radiation from the first marker area and from the second marker area.

In a further aspect of the present invention a marker for use in the aforementioned system is presented that comprises a first marker area configured to transmit light at a first wavelength, a second marker area configured to transmit light at a second wavelength, and wherein the marker is adapted for application to the detection unit.

In a further aspect of the present invention a device for use in the aforementioned system is presented that comprises a detection unit for detecting radiation received from a first marker area, configured to transmit light at a first wavelength, and from a second marker area, configured to transmit light at a second wavelength, of a marker applied to detection unit, and an analysis unit for determining the vital sign information of the subject from the detected radiation from the first marker area and from the second marker area.

In a further aspect of the present invention a method for determining vital sign information of a subject is presented that comprises the steps of detecting radiation received from a first marker area marker area, configured to transmit light at a first wavelength, and from a second marker area, configured to transmit light at a second wavelength, of a marker applied to a detection unit, and determining the vital sign information of the subject from the detected radiation from the first marker area and from the second marker area. In an embodiment, the method further comprises the step of applying the marker to the detection unit.

In yet another aspect of the present invention, there is provided a computer program which comprises program code means for causing a computer to perform the steps of the proposed method when said computer program is carried out on a computer or a processor. Further, a non-transitory computer-readable storage medium that stores therein such a computer program product, which, when executed by a processor, causes said steps of the method disclosed herein to be performed, is presented.

Preferred embodiments of the invention are defined in the dependent claims. It shall be understood that the claimed marker, device, method, computer program and medium have similar and/or identical preferred embodiments as the claimed system and as defined in the dependent claims.

The term 'vital sign' as used in the context of the present invention refers to a physiological parameter of a subject and derivative parameters. In particular, the term 'vital sign' comprises heart rate (HR) (sometimes also called pulse rate), heart rate variability (pulse rate variability), pulsatility strength, perfusion, perfusion indicator, perfusion variability, Traube Hering Mayer waves, respiratory rate (RR), body temperature, blood pressure, a concentration of a substance in blood and/or tissue, such as an oxygen saturation or a glucose level.

The term 'vital sign information' as used in the context of the present invention comprises the one or more measured vital signs as defined above. Furthermore, the term "vital sign information" comprises data referring to a physiological parameter, corresponding waveform traces or data referring to a physiological parameter over time that can serve for subsequent analysis.

The present invention is based on the idea that, instead of sequentially measuring the same area or volume of tissue at different wavelengths, the vital sign information can be determined with a marker having at least two marker areas configured to transmit light at a two different wavelengths which are measured in parallel or simultaneously. In other words, the inventor has found that it is possible to determine vital sign information from a photoplethysmographic measurement at different wavelengths with a marker that is transmissive for two wavelengths and that is attached in front of a single image sensor. Advantages are that the measurement can be performed under ambient light conditions and that no sequential narrow-band illumination at different wavelengths is required as proposed in the prior art.

According to an aspect of the present invention, a marker is proposed that comprises a first marker area configured to transmit light at a first wavelength and a second marker area configured to transmit light at a second wavelength. The first marker area and the second marker area thereby define the spatially separate areas for transmitting light at different wavelengths for determining the vital sign information. Each marker area is configured to transmit light at a different wavelength, so that the concentration of a substance can be determined based on a comparison of the light at the two different wavelengths. The use of the marker with the first and second marker areas has the advantage that a single detection unit can acquire all the required information which is beneficial for a low system cost.

Optionally, the marker comprises a further marker area separating the first and second marker area wherein the further marker area is configured to block light at a further wavelength. The wavelengths of interest also comprise non-visible wavelengths of electromagnetic radiation, including infrared and ultra-violet wavelengths.

As used herein, the term "wavelength" also refers to a band of wavelengths or wavelength portion. It is to be understood as a spectral range having a limited spectral width. For example, for an optical filter the term wavelength refers to a pass band of the filter. Hence, the term wavelength is not limited to one single wavelength but is also used for a wavelength range, for example of some nanometers or some tens of nanometers, around a center wavelength. Moreover the term wavelength in the context of a filter can also refer to multiple discontinuous spectral ranges of one and the same filter element.

As used herein, the term "detection unit" refers to a device for detecting electromagnetic radiation. It is configured to detect radiation received from the first marker area and from the second marker area. In a preferred embodiment, the detection unit is a camera with an image sensor, such as a CCD or CMOS image sensor, that comprises an array of light sensitive pixels. The output of the detection unit is referred to as radiation data. For example, the radiation data is a series of images over time, thus a video stream. The camera can be a monochrome or color camera. An RGB image sensor for a color camera comprises a color filter array with filters for the red, green and blue color channel. When using an RGB color camera, the overall filter characteristic of the system includes both the transmission characteristic of the marker areas as well as the filter characteristic of the color channels of the camera. In an embodiment the detection unit is formed by the camera included in a mobile phone.

The radiation received from the first or second marker area typically comprises two components. Firstly, the received radiation comprises light reflected at the skin surface, i.e. light that has not penetrated the tissue and does not carry information about light absorption in the tissue. Secondly, the received radiation comprises light that has penetrated into the skin and is reflected from inside the tissue. This second portion of the received radiation has a time-variant intensity due to the time-variant absorption and/or transmission of light within the tissue. The interaction of light with biological tissue is complex and includes the optical processes of (multiple) scattering, backscattering, absorption, transmission and (diffuse) reflection. The term "reflect" as used in this context is not to be construed as limited to specular reflection but comprises the aforementioned types of interaction of light with tissue and any combinations thereof.

Optionally the system further comprises a light source for emission of light at said first wavelength and/or at said second wavelength in order to ensure that sufficient light at the respective wavelength is available. Further optionally, the system comprises a control unit to control the light power such that the detection unit can be operated in its optimum operating point, in particular such that for example noise or alternatively saturation effects do not disturb the measurement. In a preferred embodiment, however, the system only uses ambient light.

The analysis unit is configured to determine the vital sign information of the subject from the detected radiation from the first marker area and from the second marker area. The analysis unit receives the radiation data from the detection unit. For determining the heart rate of the subject it is sufficient to evaluate the time-variant radiation received from a single marker area or even from bare skin outside a marker area. However, for determining the concentration of a substance, for example for determining the blood oxygen saturation or glucose level, the analysis of radiation at different wavelengths is required as described above. The analysis unit evaluates the time-variant signals from the two spatially separate marker areas and thereby evaluates two different wavelengths in parallel. For example, light received from the first marker area falls onto a first group of pixels of an image sensor that is part of the detection unit and light from the second marker area falls onto a second group of pixels of the image sensor. For a better signal-to-noise ratio, signals of pixels of a group can be combined.

In a further embodiment, the system according to the present invention further comprises a carrier element for carrying the marker. The carrier element features at least a first region to accommodate the first marker area and a second region to accommodate the second marker area. In general, the carrier element can be thought of as an element that provides mechanical support for the marker and that can be attached with screw thread, adhesive or clamp to the detection unit such that the image sensor of the detection unit receives the light at the first and second wavelengths.

In yet another embodiment, the first marker area and/or the second marker area comprise an optical filter plate that is attached to the carrier element. The optical filter plate ensures that only light of the desired wavelength or wavelength band is transmitted. The types of filter plate include absorption filters as well as dielectric filters. Advantageously, the carrier element comprises two openings and the two optical filter plates are located in said openings. Each opening is also referred to as a window or optical window. Outside the optical windows the carrier element blocks or attenuates the light.

BRIEF DESCRIPTION OF THE DRAWINGS

These and other aspects of the invention will be apparent from and elucidated with reference to the embodiments described hereinafter. In the following drawings

FIG. 4 shows a first example of a marker for attaching to a detection unit;

FIG. 5 further shows the determination of vital sign information with the system according to the present invention;

DETAILED DESCRIPTION OF THE INVENTION

Figure 1:
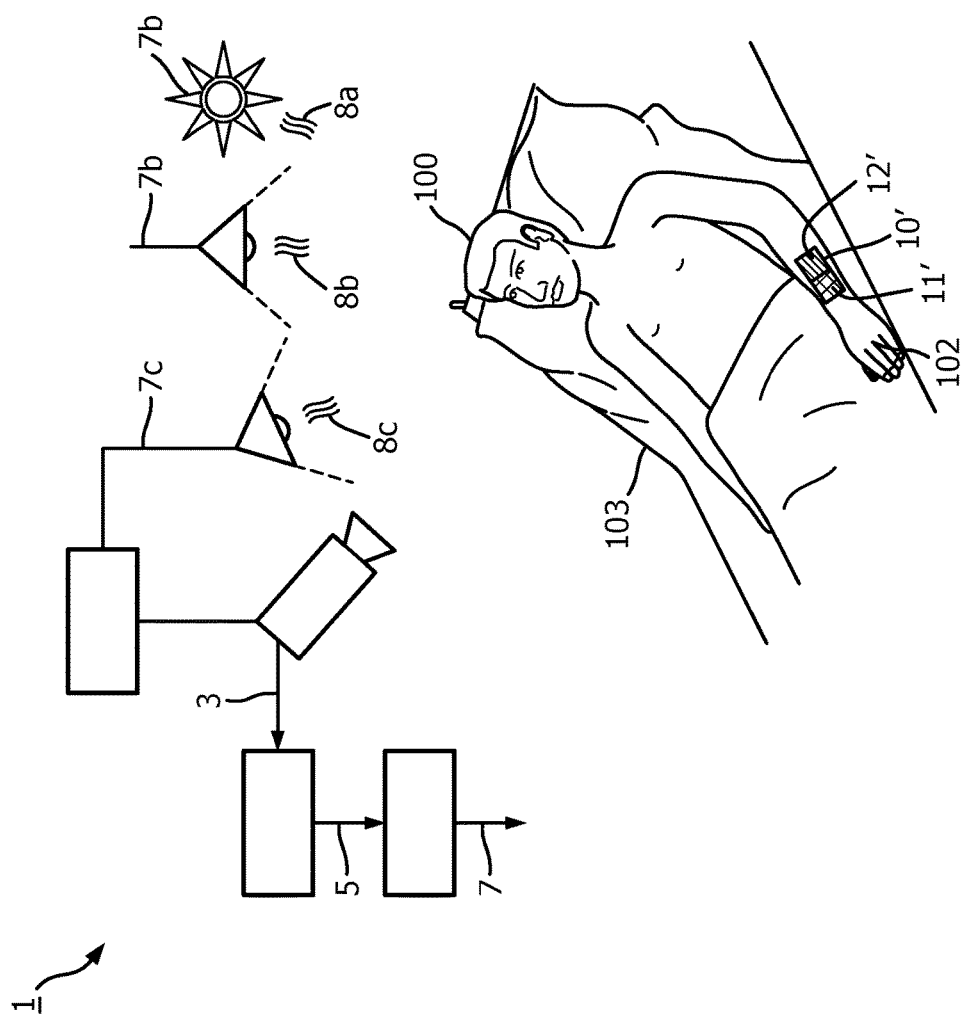
FIG. 1 shows an example of a system for determining vital sign information of a subject.

FIG. 1 shows a system 1 for determining vital sign information 7 of a subject 100. The system 1 comprises a marker 10' for application to a skin of the subject 100, a detection unit 2 and an analysis unit 6 as the basic components. In this example, the system for determining vital sign information of the subject is employed in a clinical setting, where the subject 100 lies in bed 103. The marker 10' further comprises a first marker area 11' configured to transmit light at a first wavelength and a second marker area 12' configured to transmit light at a second wavelength. The detection unit 2 is adapted to detect radiation received from the first marker area 11' and from the second marker area 12 of the marker 10'. In this example, the detection unit 2 is connected to an optional image processing unit 4. The detection unit 2 provides radiation data 3 that represents the detected radiation, to the image processing unit 4 in form of a video stream. The image processing unit 4 identifies the first marker area 11 and the second marker area 12 in the radiation data 3. The image processing unit 4 in turn is connected to the analysis unit 6. The image processing unit 4 provides preprocessed radiation data 5 to the analysis unit 6. The preprocessed radiation data 5 in this example comprises information about which region of the images of the video stream of the radiation data 3 depict the first marker area 11 and the second marker area 12. The analysis unit 6 in turn determines the vital sign information 7 of the subject from time-variant intensity in the first marker area 11 and in the second marker area 12. In this example, the vital sign information comprises a heart rate and a blood oxygen saturation.

According to the insight of the inventor the marker may also be applied to the detection unit 2 such that the light reflected by the skin 102 of the patient is received by an image sensor included in the detection unit after passing through the first and second marker area. Preferably the marker with the first and second marker areas is positioned close to the image sensor such that a first group of pixels receives the reflected light filtered by the first marker area and a second group of pixels receives the reflected light filtered by the second marker area.

The present invention is based on the idea to move the marker with two or more optical filters from the skin (as shown in FIG. 1) to the camera 2 for generating a biometrical signal (also called vital sign) of a living being. While in conventional cameras mainly visible (including some infrared) light is sensed by an image sensor, e.g. an RGB sensor or monochrome sensor, according to the present invention it is proposed to use a set of filters that transmit incident visible light for a corresponding set of predetermined wavelengths such that groups of pixels of the image sensor receive a predetermined wavelength of said set of predetermined wavelengths. In other words, the spectral characteristics of the camera are modified by placing the marker for blocking incident visible light in the optical path of the camera so that only light of a first wavelength (for example 660 nm) is transmitted through a first optical filter and hits a first portion of the image sensor and light of a second wavelength (for example 900 nm) passing through a second optical filter hits a second portion of the image sensor. The image sensor generates at least two different color signals, each one resulting from a corresponding portion of the image sensor.

These color signals are further processed to extract a biometrical signal from the received reflected light. The result is an inexpensive and rather simple camera which is suitable for biometrical signal detection, for example for SpO2 monitoring.

Figure 2:
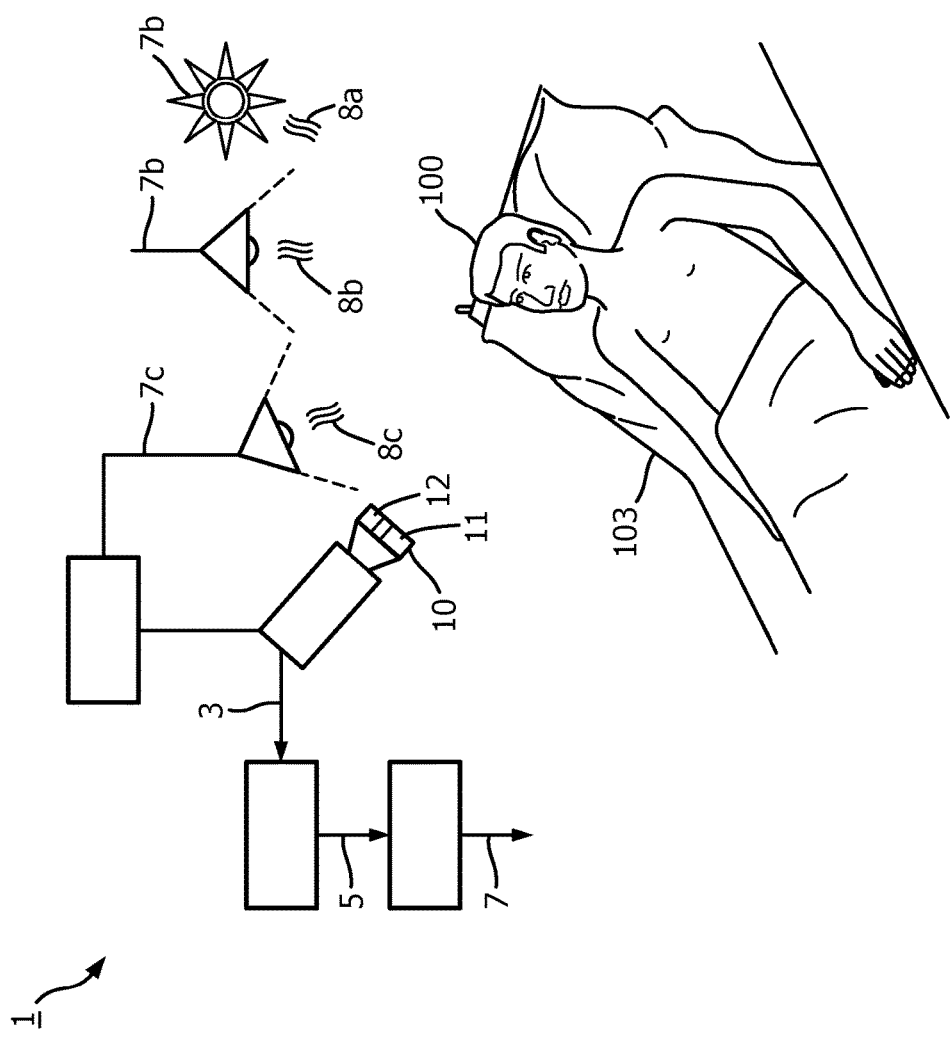
FIG. 2 shows an exemplary embodiment of the system for determining vital sign information of a subject according to the present invention.

FIG. 2 shows an exemplary embodiment of a system 1 for determining vital sign information 7 of a subject 100 according to the present invention in which the marker has been moved from the skin of the patient and has been applied on a receiving end of the detection unit. The system 1 comprises a marker 10 for application to a detection unit 2, the detection unit 2 and an analysis unit 6 as the basic components. In this example, the system for determining vital sign information of the subject is employed in a clinical setting, where the subject 100 lies in bed 103. The marker 10 further comprises a first marker area 11 configured to transmit light at a first wavelength and a second marker area 12 configured to transmit light at a second wavelength. The detection unit 2 is adapted to detect radiation received from the first marker area 11 and from the second marker area 12 of the marker 10. In this example, the detection unit 2 is connected to an optional image processing unit 4. The detection unit 2 provides radiation data 3 that represents the detected radiation, to the image processing unit 4 in form of a video stream. The image processing unit 4 identifies the data obtained from the first group of pixels and the second group of pixels in the radiation data 3. The image processing unit 4 in turn is connected to the analysis unit 6. The image processing unit 4 provides preprocessed radiation data 5 to the analysis unit 6. The preprocessed radiation data 5 in this example comprises information about which group of pixels of the images of the video stream of the radiation data 3 depict the first group of pixels and the second group of pixels. The analysis unit 6 in turn determines the vital sign information 7 of the subject from time-variant intensity in the first group of pixels resulting from reflected light passing through the first marker area 11 and in the second group of pixels resulting from reflected light passing through the second marker area 12. In this example, the vital sign information comprises a heart rate and a blood oxygen saturation.

The image processing unit 4 for identifying the first marker area 11 and the second marker area can also be incorporated into the analysis unit 6. Alternatively, the radiation data 3 is directly provided to the analysis unit 6.

In the shown example, the marker 10 is directly applied to the detection unit 2 such that the light received by an image sensor of the detection unit passes through the first and second marker area.

The scenery is illuminated by a source of radiation, such as sunlight 7a or an artificial light source 7b. The radiation source 7a, 7b directly or indirectly emits radiation 8a, 8b towards the subject 100. In addition, or in the alternative, the system 1 can also comprise an optional system light source 7c that emits light 8c towards the subject 100. The use of a system light source 7c is particularly beneficial if the ambient light sources 7a, 7b do not provide sufficient light or if the spectrum of the ambient light sources 7a, 7b does not provide sufficient power at the first wavelength and at the second wavelength.

An optional control unit 9 is adapted to control the sensitivity of the detection unit 2 and/or to control the power of the system light source 7c. Because the dynamic range of a detector or image sensor that is used as the detection unit 2 is limited, shutters and electronic offsets may have to be adjusted according to the lighting situation in the observed scene. The system light source 7c can be part of a control loop which sets an optimal operating point of the image sensor of the detection unit 2. Optimal in this context refers to an output signal without signal clipping, no saturation of individual detectors of the image sensors and a good signal-to-noise ratio at least for the detector or image sensor area corresponding to first and/or second marker area.

Figure 3:
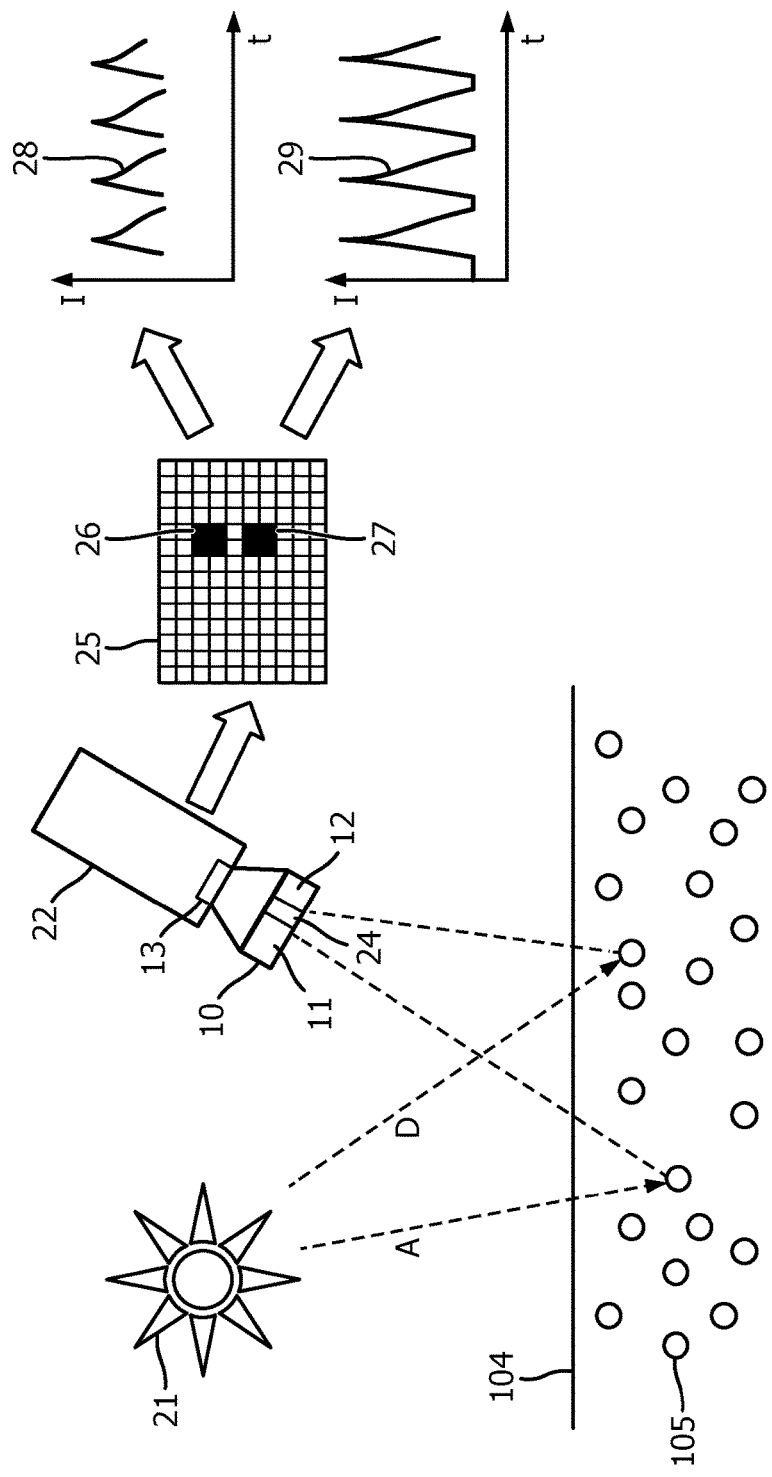
FIG. 3 shows the determination of vital sign information with the system according to the present invention.

FIGS. 3, 4 and 5 illustrate the determination of vital sign information of a subject with the system 1 according to the present invention. FIG. 3 shows a light source 21, a detection unit 22 and a marker, shown in more detail in FIG. 4 from the front and in FIG. 5 from the side, having a first marker area 11 and a second marker area 12. The marker is applied to a detection unit 22, for example in front of the lens 13. The detection unit comprises the lens and an image sensor 14 which is shown in FIG. 5. The tissue comprises blood vessels 105.

In this embodiment, the light source 21 emits light at least a first wavelength $\lambda_1$ and a second wavelength $\lambda_2$. The first marker area 11 is configured to transmit light at the first wavelength, wherein said first wavelength corresponds to the first wavelength of the light source 21. The second marker area 12 is configured to transmit light at the second wavelength, wherein said second wavelength corresponds to the second wavelength of the light source 21. FIG. 3 sketches a light ray A at the first wavelength and a light ray D at the second wavelength. Since the first marker area 23 is configured to transmit light at the first wavelength, the ray A penetrates into the skin 104 of the subject 100. Some of the light is absorbed within the skin 104, while some of the light is reflected or scattered in the tissue and reaches the detection unit 22. The absorption and/or reflection characteristic is time-variant and represents the time-variant perfusion of the tissue 104 with its blood vessels 105.

The detection unit 22 comprises receiving optics, for example a receiver lens 13, and an array 25 of photo detectors or pixels that form an image sensor 14. Light that is received from the first marker area 11 is imaged onto a first group or array of pixels 26. Correspondingly, light received from the second marker area 12 is imaged onto a second group of pixels 27. The marker may further have a third marker area 24, see FIGS. 4 and 5, which blocks or attenuates all wavelengths for which the image sensor 14 is sensitive. The array of pixels 25 further comprises a third group 23 pixels separating the first and the second group of pixels.

Since the absorption of light in the tissue 104 is time-variant, the light intensity incident on the image sensor of the detection unit 22 is also time-variant. The time-variant intensity on the area of pixels 26 is depicted by curve 28. The time-variant intensity incident on the group of pixels 27 is depicted by curve 29.

Since the first marker area is configured to transmit light at the first wavelength only, light at the second wavelength does not pass the first marker area 11 and is not imaged to the second group or array of pixels. Likewise since the second marker area 12 is configured to transmit light at the second wavelength only, light at the first wavelength does not pass the second marker area 12 and is not imaged to the first group or array of pixels. Nonetheless, due to a distance between the marker 10 and the lens 13 some of the light at the first wavelength can reach the second group of pixels 27 and some of the light at the second wavelength can reach the first group of pixels 26, resulting in some blending. To prevent the blending the first marker area 11 and second marker area 12 are separated from each other by the third marker area 24 which blocks the first and the second wavelength. Further the first group of pixels is preferably separated from the second group of pixels by the third group 23 of pixels. The intensity modulation depicted by curve 28 is due to the time-variant reflection in the tissue 104 at the first wavelength. The intensity modulation depicted by curve 29 is thus due to the time-variant reflection in the tissue 104 at the second wavelength.

The pulse rate of the subject can be directly determined from the time-variant intensity in one of the curves 28 or 29. However for determining the blood oxygen saturation by photoplethysmography at least two wavelengths are required, as exemplarily explained below.

Contact pulse oximeters typically transmit red (R) and infrared (IR) (or, more precisely, in many cases near infrared) light through a vascular tissue of the subject of interest. The respective light portions (R/IR) can be transmitted and detected in an alternating (fast-switching) manner. Given that the respective spectral portions are differently absorbed by oxygenated hemoglobin ($HbO_2$) and reduced hemoglobin (Hb), blood oxygen saturation eventually can be processed. An oxygen saturation ($SO_2$) estimation algorithm can make use of a ratio of the signals related to the red and the infrared portion. Furthermore, the algorithm can consider a non-pulsatile signal component. Typically, the PPG signal comprises a DC component and a relatively small pulsatile AC component as schematically illustrated in FIG. 5. Furthermore, $SO_2$ estimation generally involves an empirically derived calibration factor applied to the processed values. Typically, the calibration factor (or, calibration curve) is determined upon reference measurements involving invasive blood oxygen saturation measurements. A calibration factor is required since a PPG device basically detects a ratio of (spectral) signal portions which has to be transferred into a blood oxygen saturation value which typically involves a ratio of $HbO_2$ and Hb. For instance, but not intended to limit the present disclosure, blood oxygen saturation estimation can be based on the following general equation:

$$SO_2\ [\%] = \frac{[HbO_2]}{[HbO_2] + [Hb]} \times 100\%, \qquad (1)$$

whereas PPG devices merely mediately detect $HbO_2$ and Hb from the spectral response at least two wavelengths.

Generally, the measured intensity curve 28, 29 as a characteristic signal is considered to contain a considerably constant (DC) portion and an alternating (AC) portion superimposing the DC portion. Applying signal processing measures, the AC portion can be extracted and, furthermore, compensated for disturbances. For instance, the AC portion of the characteristic signal can comprise a dominant frequency which can be highly indicative of the subject's 100 vascular activity, in particular the heart beat. Still, the characteristic signal, in particular the AC portion, can be indicative of further vital parameters. In this connection, the detection of arterial blood oxygen saturation is an important field of application. As indicated above, basically, arterial blood oxygen saturation-representative values can be computed taking into account the behavior of the AC portion of the characteristic signal at distinct spectral portions thereof. In other words, a degree of arterial blood oxygen saturation can be reflected in different radiation absorbance at blood vessels. Furthermore, one can make use of the fact that the difference in absorbance due to the grade of oxygenation also varies significantly across different spectral portions. Moreover, also the DC portion of the signal can be utilized for blood oxygen saturation detection. Typically, the DC component represents the overall light absorption of the tissue, venous blood, and non-pulsatile arterial blood. By contrast, the AC component may represent the pulsatile arterial blood's absorption. Consequently, the determination of arterial blood oxygen saturation ($SaO_2$) can be expressed as:

$$SaO_2 = C \cdot \frac{(AC/DC)_{red}}{(AC/DC)_{infrared}}, \qquad (2)$$

where C is a calibration parameter. C may stand for a large variety of calibration parameters applicable to the AC/DC relationship and should therefore not be interpreted in the strict algebraic sense of equation (2). C may, for example, represent a fixed constant value, a set of fixed constants or an adjustable calibration parameter. By way of example, another exemplary $SaO_2$ derivation model can be expressed as:

$$SaO_2 = C_1 + C_2 \cdot \frac{(AC/DC)_{red}}{(AC/DC)_{infrared}}, \qquad (3)$$

where $C_1$ and $C_2$ can be considered calibration parameters of a linear approximation. In an exemplary embodiment, the signal calibration parameter determination can be directed to adjust or adapt the parameter $C_1$. Still, in the alternative, $SaO_2$ derivation may also be based on value tables deposited in (or accessible by) the device 1. The value tables (or: data bases) may provide for a discrete representation of the relationship between detected PPG signals and the desired calibration parameter. Also in that case an adaptable calibration parameter may be applied to improve the accuracy of the vital parameter determination.

It should be understood that the equations (2) and (3) are primarily presented for illustrative purposes. They should not be construed as limiting the scope of the present disclosure. In practice, the skilled person may determine and establish further appropriate $SaO_2$ derivation models. Alternative wavelength combinations, for example green and red, can be used depending on the substance to be detected. While the measurement of $SaO_2$ has been described in detail, this is to be understood as an example for the general concept of measuring the concentration of a substance in blood and/or tissue.

Figure 6:
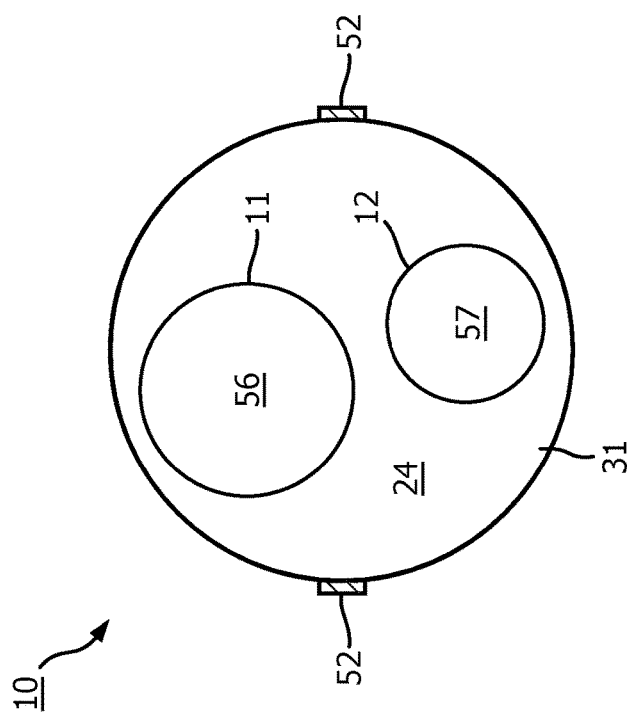
FIG. 6 shows a first example of a marker.

A marker may have any geometry and also the marker areas may have different shapes. FIG. 6 shows a more detailed embodiment of a marker for use in a system 1 for determining vital sign information of a subject according to the present invention. The marker 10 features marker areas 11, 12, each marker area configured to transmit light at a different wavelength, and a intransparent (for wavelengths that are detectable by the image sensor) marker area 24 formed by the carrier element 31. The carrier element 31 carries the marker 10 with its elements and provides mechanical stability. In this embodiment, the carrier element 31 further comprises attachment means such as a srew thread, clamp, strap or adhesive to allow the marker 10 to be attached to the detection unit. The carrier element is made from a material that does not transmit light and features openings or windows at the positions of the marker areas 11, 12.

In each of the windows 11, 12, an optical filter plate 56, 57 is placed wherein the filter plate 11 is configured to transmit light at a first wavelength and the filter plate 12 is configured to transmit light at a second wavelength. For example, the first marker area 11 is configured to transmit infrared light and the second marker area 12 is configured to transmit red light. The optical windows for the first and second marker areas 11, 12 of the embodiment of the marker 10 shown in FIG. 6 are optimized depending on the expected signal strength. For example, the signal at a first required wavelength, for example green, is stronger than signal at the second required wavelength, for example red. Thus, the overall second marker area 12 is increased with respect to the overall first marker area 11 to achieve a similar signal strength at both wavelengths.

Figure 7:
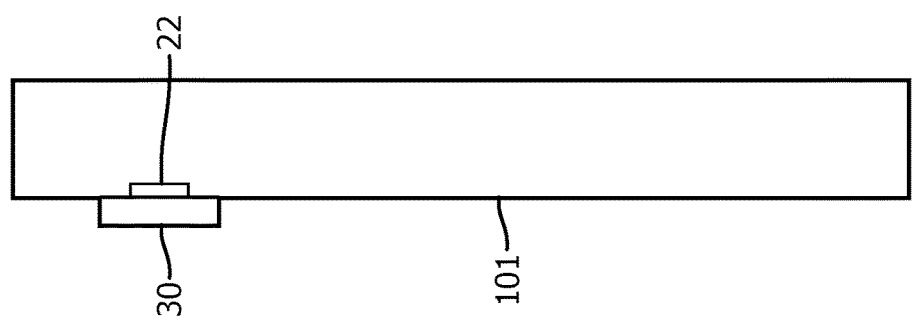
FIG. 7 shows a second embodiment of a system for determining vital sign information of a subject.

FIG. 7 shows a further embodiment of a system for determining vital sign information of a subject comprising a mobile phone or smart phone 101 with the above described marker 30 attached thereto. The mobile phone 101 comprises a detection unit 22 for detecting radiation received from the first marker area and from the second marker area of the marker. The detection unit 22 comprises a lens and image sensor chip. The mobile phone further comprises a processor that includes the analysis unit for determining the vital sign information of the subject from the detected radiation from the first marker area and from the second marker area. In a further embodiment the system for determining vital sign information of a subject is included in a pair of glasses.

Figure 8:
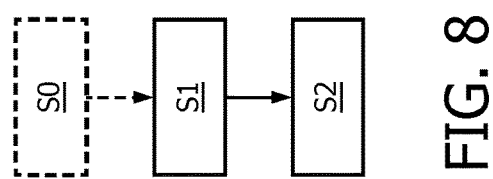
FIG. 8 illustrates a method for determining vital sign information of a subject.

FIG. 8 illustrates a method for determining vital sign information of a subject comprising:
a first step S1 of detecting radiation received from a first marker area marker area, configured to transmit light at a first wavelength, and from a second marker area, configured to transmit light at a second wavelength, of a marker applied to a detection unit for detecting radiation received from the first filter area and the second filter area, and
a second step S2 of determining the vital sign information of the subject from the detected radiation from the first marker area and from the second marker area. The method may be implemented in program code. When the program code runs on the processor included in the mobile phone 101 results the processor to perform the function of the analysis unit for determining the vital sign information of the subject from the detected radiation from the first marker area and from the second marker area. In a further embodiment of the method the first step is preceded by a step S0 of applying the marker to the detection unit.

By way of example, the present invention can be applied in the field of health care, e.g. unobtrusive remote patient monitoring, general surveillances, security monitoring and so-called lifestyle environments, such as fitness equipment, or the like. Applications may include monitoring of oxygen saturation (pulse oximetry), heart rate, blood pressure, cardiac output, changes of blood perfusion, assessment of autonomous functions, and detection of peripheral vascular diseases.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system for determining vital sign information of a subject comprising:
a camera including a lens and an image sensor;
a marker including a first marker area configured to transmit light at a first wavelength and a second marker area configured to transmit light at a second wavelength, the first marker area comprising a first optical filter plate and the second marker area comprising a second optical filter plate, the first and second filter plates being non-rotatably attached to the carrier element;
a carrier element, the marker being stationarily mounted to the carrier element, the carrier element being stationarily mounted to the camera such that light transmitted through the first marker area hits a first portion of the image sensor and light transmitted through the second marker area hits a second portion of the image sensor;
wherein the image sensor generates at least a first color signal resulting from the first portion of the image sensor and a second color signal resulting from the second portion of the image sensor, and
a processor configured to determine the vital sign information of the subject from the first and second color signals.

2. The system according to claim 1, including an adhesive configured to attach the carrier to the camera.

3. The system according to claim 1,
wherein the first and second marker areas are separated from each other by a third marker area configured to block light.

4. The system according to claim 1 wherein the camera is integrated in a mobile phone.

5. The system according to claim 4 wherein the carrier element is configured to be stationarily and non-rotatably attached to the mobile phone.

6. The system according to claim 5 wherein the first filter area and the second filter area comprise first and second optical filter plates attached to the carrier element.

7. The system according to claim 6 wherein the carrier element further comprises an adhesive, a thread or a clamp for enabling the attachment of the carrier element to the camera.

8. A system configured for determining vital sign information with a mobile phone including a camera having a lens configured to focus light received through the lens on an array of detector pixels and a processor configured to process data, the system comprising:
a first optical filter plate configured to pass light of a first wavelength and block light of other wavelengths;

a second optical filter plate configured to pass light of a second wavelength and block light of other wavelengths;

a carrier, the first and second optical filter plates being stationarily mounted in the carrier, the carrier being configured for attachment to the mobile phone adjacent the lens such that light of the first color passing through the first filter is received by a first group of the array of detector pixels and light of the second color is received by a second group of the array of detector pixels, the second group being displaced from the first group; and software configured to program the processor to determine the vital sign information from data received from the first and second groups of detector pixels.

9. The system according to claim 8, wherein the mobile phone includes a display and the programmed processor is further programmed to at least one of store the vital sign information and control the display to display the vital sign information.

10. The system according to claim 8, wherein the processor includes a non-transitory computer-readable medium configured to store the software.

11. The system according to claim 8, further including a non-transitory computer-readable medium storing the software.

12. The system according to claim 8, wherein the carrier includes a marker area which blocks all but the first and second groups of pixels from receiving wavelengths of light that the pixels are sensitive to.

13. The system according to claim 8, further including:
attaching means for attaching the carrier stationarily and non-rotatably relative to the mobile phone such that the first and second optical filter plates do not move relative to the lens and the array of detector pixels.

14. A method for determining vital sign information of a subject comprising the steps of
passing light from a patient through a first marker area marker area, configured to transmit light at a first wavelength, and through a second marker area, configured to transmit light at a second wavelength;

with a camera included in a mobile phone in which the camera comprises a lens and an image sensor, focusing the light transmitted through the first marker area on a first portion of the image sensor and the light transmitted through the second marker area on a second portion of the image sensor, the first and second portions of the sensor being different and separated from each other;

generating a first signal with the first portion of the image sensor and a second signal from the second portion of the image sensor, determining the vital sign information of the subject from the first and second signals, wherein the first and second marker areas and the lens and the image sensor remain in a fixed, non-rotating relationship relative to each other during the transmitting of light through the first and second marker areas.

15. The method according to claim 14 further comprising:
applying the marker to the camera.

* * * * *